United States Patent
Milsom et al.

(10) Patent No.: US 9,649,100 B2
(45) Date of Patent: May 16, 2017

(54) METHOD AND APPARATUS FOR STRAIGHTENING AND FLATTENING THE SIDE WALL OF A BODY LUMEN OR BODY CAVITY SO AS TO PROVIDE THREE DIMENSIONAL EXPOSURE OF A LESION OR ABNORMALITY WITHIN THE BODY LUMEN OR BODY CAVITY, AND/OR FOR STABILIZING AN INSTRUMENT RELATIVE TO THE SAME

(75) Inventors: Jeffrey Milsom, New York, NY (US); Howard Riina, Scarsdale, NY (US); John Fredrick Cornhill, New York, NY (US); Robert Andrews, Norfolk, MA (US); Edward Dickinson, Littleton, MA (US)

(73) Assignee: Cornell University, Ithaca, NY (US)

( * ) Notice: Subject to any disclaimer, the term of this patent is extended or adjusted under 35 U.S.C. 154(b) by 1230 days.

(21) Appl. No.: 12/511,256

(22) Filed: Jul. 29, 2009

(65) Prior Publication Data
US 2010/0094327 A1    Apr. 15, 2010

Related U.S. Application Data

(60) Provisional application No. 61/137,361, filed on Jul. 30, 2008.

(51) Int. Cl.
*A61M 29/00* (2006.01)
*A61B 17/02* (2006.01)
(Continued)

(52) U.S. Cl.
CPC ...... *A61B 17/0218* (2013.01); *A61B 1/00087* (2013.01); *A61F 2/86* (2013.01);
(Continued)

(58) Field of Classification Search
CPC .............................. A61B 17/0218; A61B 1/01
(Continued)

(56) References Cited

U.S. PATENT DOCUMENTS

| 5,071,407 A | 12/1991 | Termin et al. |
| 5,192,286 A | 3/1993 | Phan et al. |

(Continued)

FOREIGN PATENT DOCUMENTS

| JP | 2-289240 | 11/1990 |
| JP | 411299795 A | 11/1999 |

(Continued)

*Primary Examiner* — Diane Yabut
(74) *Attorney, Agent, or Firm* — Pandiscio & Pandiscio (57) ABSTRACT

Apparatus for straightening and flattening a side wall of a body lumen or body cavity so as to provide three dimensional exposure of an abnormality within the body lumen, and simultaneously providing for the stabilization of the working end of an endoscope or surgical tool, the apparatus comprising a deployable hoop expander comprising a structure defining a volume and being configured so as to be transitionable between a reduced cross-sectional configuration for easy insertion into a body lumen and an expanded cross-sectional configuration for engaging, straightening and flattening the side wall of the body lumen, whereby to provide three dimensional exposure of the abnormality within the body lumen, the deployable hoop expander being configured for simultaneously providing for the docking of the end of the endoscope or other instrument so as to stabilize the same for endoscopic viewing and/or therapy.

41 Claims, 10 Drawing Sheets

(51) Int. Cl.
 *A61F 2/86* (2013.01)
 *A61B 1/00* (2006.01)
 *A61F 2/88* (2006.01)
 *A61F 2/91* (2013.01)
 *A61F 2/95* (2013.01)
 *A61F 2/04* (2013.01)

(52) U.S. Cl.
 CPC . *A61F 2/88* (2013.01); *A61F 2/91* (2013.01); *A61F 2/95* (2013.01); *A61F 2002/045* (2013.01); *A61F 2002/9528* (2013.01); *A61F 2230/008* (2013.01); *A61F 2250/0059* (2013.01)

(58) Field of Classification Search
 USPC .......................................................... 606/191
 See application file for complete search history.

(56) References Cited

U.S. PATENT DOCUMENTS

| | | | |
|---|---|---|---|
| 5,496,365 A | 3/1996 | Sgro | |
| 5,643,312 A | 7/1997 | Fischell et al. | |
| 5,795,289 A * | 8/1998 | Wyttenbach | 600/207 |
| 5,797,888 A * | 8/1998 | Yoon | 604/530 |
| 5,906,621 A | 5/1999 | Secrest et al. | |
| 6,176,873 B1 | 1/2001 | Ouchi | |
| 6,582,461 B1 * | 6/2003 | Burmeister et al. | 623/1.18 |
| 7,087,062 B2 | 8/2006 | Dhindsa | |
| 7,122,003 B2 | 10/2006 | Nakao | |
| 2003/0225432 A1 * | 12/2003 | Baptiste | A61B 17/0218 606/191 |
| 2003/0225433 A1 | 12/2003 | Nakao | |
| 2005/0070949 A1 | 3/2005 | Bakos et al. | |
| 2005/0085842 A1 | 4/2005 | Eversull et al. | |
| 2005/0131403 A1 | 6/2005 | Chang | |
| 2005/0209627 A1 | 9/2005 | Kick et al. | |
| 2005/0267491 A1 | 12/2005 | Kellett et al. | |
| 2006/0041270 A1 | 2/2006 | Lenker et al. | |
| 2006/0135981 A1 | 6/2006 | Lenker et al. | |
| 2006/0184048 A1 | 8/2006 | Saadat | |
| 2006/0270978 A1 * | 11/2006 | Binmoeller et al. | 604/104 |
| 2007/0208367 A1 | 9/2007 | Fiorella et al. | |
| 2008/0033451 A1 * | 2/2008 | Rieber et al. | 606/114 |
| 2008/0146872 A1 | 6/2008 | Gruber et al. | |

FOREIGN PATENT DOCUMENTS

| | | |
|---|---|---|
| WO | WO 2005/048828 | 6/2005 |
| WO | WO 2007/083305 | 7/2007 |

* cited by examiner

METHOD AND APPARATUS FOR STRAIGHTENING AND FLATTENING THE SIDE WALL OF A BODY LUMEN OR BODY CAVITY SO AS TO PROVIDE THREE DIMENSIONAL EXPOSURE OF A LESION OR ABNORMALITY WITHIN THE BODY LUMEN OR BODY CAVITY, AND/OR FOR STABILIZING AN INSTRUMENT RELATIVE TO THE SAME

REFERENCE TO PENDING PRIOR PATENT APPLICATION

This patent application claims benefit of prior U.S. Provisional Patent Application Ser. No. 61/137,361, filed Jul. 30, 2008 by Jeffrey Milsom et al. for METHOD AND APPARATUS FOR STRAIGHTENING AND FLATTENING THE SIDE WALL OF A BODY LUMEN OR BODY CAVITY SO AS TO PROVIDE THREE DIMENSIONAL EXPOSURE OF A LESION OR ABNORMALITY WITHIN THE BODY LUMEN OR BODY CAVITY, AND/OR FOR STABILIZING AN INSTRUMENT RELATIVE TO THE SAME, which patent application is hereby incorporated herein by reference.

FIELD OF THE INVENTION

This invention relates to surgical methods and apparatus in general, and more particularly to surgical methods and apparatus for straightening and flattening the side wall of a body lumen or body cavity so as to provide three dimensional exposure of a lesion or abnormality within the body lumen or body cavity, and/or for stabilizing an instrument relative to the same.

BACKGROUND OF THE INVENTION

The human body comprises many different lumens and cavities. By way of example but not limitation, the human body comprises lumens such as the gastrointestinal (GI) tract, blood vessels, lymph nodes, the ureter, etc. By way of further example but not limitation, the human body comprises cavities such as the abdomen, the chest, the nasal sinuses, the bladder, etc.

In many cases, it may be desirable to endoscopically examine and/or treat a disease process or abnormality within or on the side wall of a body lumen and/or body cavity. By way of example but not limitation, it may be desirable to examine the lumen or side wall of the gastrointestinal tract for lesions and, if a lesion is found, to biopsy, remove, and/or treat the lesion.

The endoscopic examination and/or treatment of the side wall of a body lumen and/or body cavity can be complicated by the geometry of the side wall of the body lumen or body cavity. By way of example but not limitation, the intestine is an elongated organ having an inner lumen characterized by frequent turns and side walls characterized by numerous folds. It can be difficult to examine and/or treat a lesion formed on the side wall of the intestine due to this varying side wall geometry.

It would be advantageous to provide an endoscopic device capable of straightening and flattening the side wall of a body lumen or body cavity so as to better present the side wall tissue for examination and/or treatment during an endoscopic procedure.

It would also be advantageous to provide an endoscopic device capable of steadying, or maintaining in a fixed position, the tip(s) or working end(s) of an instrument (or instruments) inserted into a body space.

SUMMARY OF THE INVENTION

The present invention comprises the provision and use of a novel endoscopic device capable of straightening and flattening the side wall of a body lumen or body cavity so as to better expose or present the side wall tissue in all dimensions for examination and/or treatment during an endoscopic procedure.

The present invention also comprises the provision and use of a novel endoscopic device capable of steadying or stabilizing the tip or working end of an instrument or several instruments.

In one preferred form of the present invention, there is provided apparatus for straightening and flattening a side wall of a body lumen or body cavity so as to provide three dimensional exposure of a lesion or abnormality within the body lumen or body cavity, the apparatus comprising:

a deployable hoop expander comprising a longitudinally-extending structure defining a volume;

the deployable hoop expander being configured so as to be transitionable between (i) a reduced cross-sectional configuration, and (ii) an expanded cross-sectional configuration, whereby the deployable hoop expander can be configured in its reduced cross-sectional configuration for easy insertion into a body lumen, and it can thereafter be re-configured into its expanded cross-sectional configuration so as to engage, expose, straighten and flatten the side wall of the body lumen, whereby to provide three dimensional exposure of the lesion or abnormality within the body lumen or body cavity.

In one preferred form of the present invention, the deployable hoop expander comprises an open lattice configuration allowing access to the lumen or side wall of the body lumen or body cavity.

And in another preferred form of the present invention, the deployable hoop expander is configured so as to allow an instrument (or instruments) to dock with the deployable hoop expander, whereby to permit the deployable hoop expander to steady or stabilize the tip(s) or working end(s) of the instrument(s).

In another preferred form of the present invention, there is provided a method for straightening and flattening a side wall of a body lumen or body cavity so as to provide three dimensional exposure of a lesion or abnormality within the body lumen or body cavity, the method comprising:

providing a deployable hoop expander;
the deployable hoop expander comprising a longitudinally-extending structure defining a volume; and
the deployable hoop expander being configured so as to be transitionable between (i) a reduced cross-sectional configuration, and (ii) an expanded cross-sectional configuration;
configuring the deployable hoop expander in its reduced cross-sectional configuration;
advancing the deployable hoop expander into a body lumen; and
re-configuring the deployable hoop expander into its expanded cross-sectional configuration so as to engage, expose, straighten and flatten the side wall of the body lumen, whereby to provide three dimensional exposure of the lesion or abnormality within the body lumen or body cavity.

In one preferred form of the present invention, the deployable hoop expander comprises an open lattice configuration allowing access to the side wall of the body lumen or body cavity.

And in one preferred form of the present invention, the deployable hoop expander is configured so as to allow an instrument (or instruments) to dock with the deployable hoop expander, whereby to permit the deployable hoop expander to steady or stabilize the tip(s) or working end(s) of the instrument(s).

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PRESENT INVENTION

The Novel Endoscopic (or Surgical) Device in General

The present invention comprises the provision and use of a novel endoscopic (or surgical) device capable of straightening and flattening the side wall of a body lumen or body cavity so as to better present the side wall tissue for examination and/or treatment during an endoscopic or surgical procedure and/or to stabilize an instrument relative to the same.

More particularly, the present invention comprises the provision and use of a novel endoscopic/surgical device for facilitating the alignment and presentation of the side wall of a body lumen or body cavity during an endoscopic or other surgical procedure, and/or for stabilizing an instrument relative to the same. In this respect, the term "endoscopic procedure" is intended to mean substantially any minimally-invasive procedure, diagnostic or surgical, for accessing the inside of a vessel or organ within the body for purposes of viewing, biopsying and/or treating the tissue (including removing a lesion), and the term surgical procedure is intended to mean substantially any medical operative procedure performed on the body. The novel endoscopic/surgical device of the present invention (hereinafter sometimes referred to, for convenience, as simply an endoscopic device) is adapted to straighten and flatten bends and/or curves and/or folds in the side wall of the vessel or organ, and can provide a platform for the performance of numerous procedures within the vessel or organ, including the possible docking and/or fixation of an endoscope and/or other surgical instruments within the vessel or organ.

Figures 1, 2, 3:
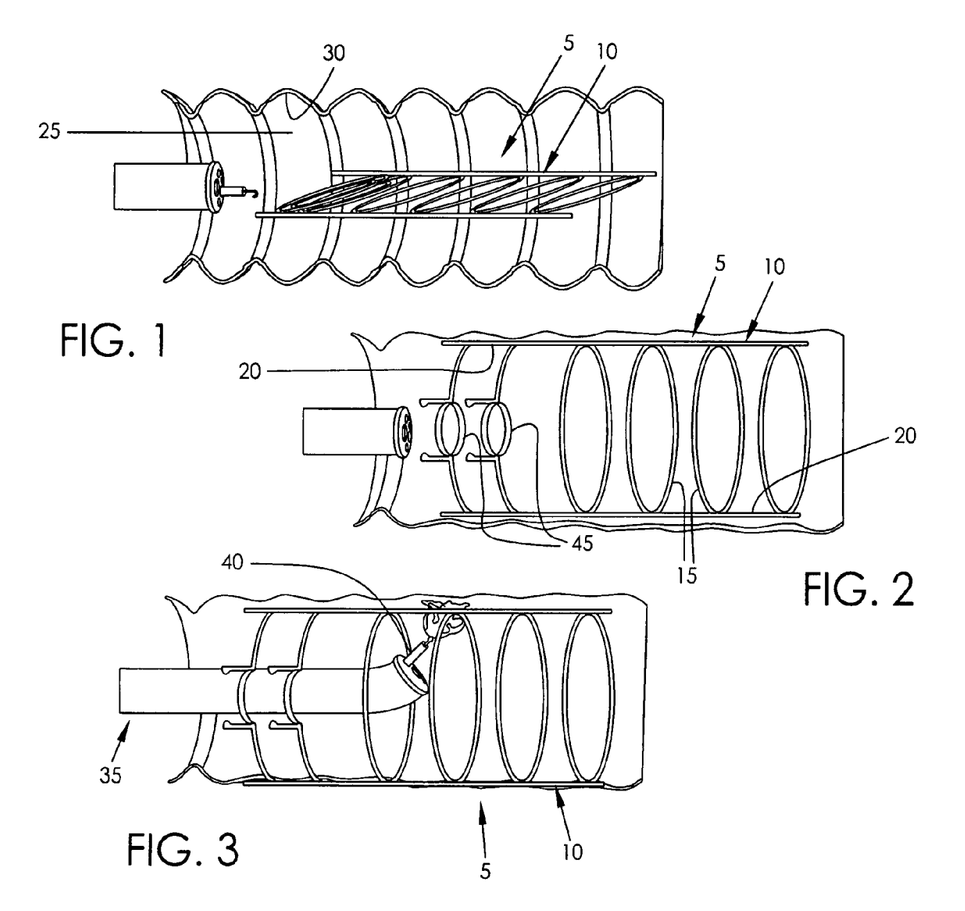
FIGS. 1-3 are schematic views showing a novel endoscopic device formed in accordance with the present invention, wherein the novel endoscopic device is being deployed in a body lumen so as to straighten and flatten the side wall of the body lumen so as to provide three dimensional exposure of a lesion or abnormality within the body lumen or body cavity and/or to provide stability to the working end of an instrument.

In accordance with the present invention, and looking now at FIGS. 1-3, there is shown an endoscopic device 5 capable of straightening and flattening the side wall of a body lumen or body cavity so as to better present the side wall tissue for examination and/or treatment during an endoscopic procedure, and/or for stabilizing an instrument relative to the same. More particularly, endoscopic device 5 generally comprises a deployable hoop expander 10 which generally comprises a plurality of parallel rings 15 connected together by a plurality of struts 20. Deployable hoop expander 10 is configured so as to be transitionable between (i) a reduced cross-sectional configuration (FIG. 1) wherein the planes of the parallel rings 15 are disposed at an acute angle (when seen in side view) to the longitudinal axis of deployable hoop expander 10, and (ii) an expanded cross-sectional configuration (FIG. 2) wherein the planes of the parallel rings 15 are disposed perpendicular (when seen in side view) to the longitudinal axis of deployable hoop expander 10. As a result of this construction, deployable hoop expander 10 can be configured in its reduced cross-sectional configuration for easy insertion into a body lumen (e.g., a vascular lumen, an organ lumen, etc.) 25 (FIG. 1), and it can thereafter be re-configured into its expanded cross-sectional configuration so as to engage, expose, straighten and flatten the side wall 30 of body lumen 25 (FIG. 2). This engagement, straightening and flattening of side wall 30 of body lumen 25 better presents the side wall tissue for examination and/or treatment during an endoscopic procedure, e.g., such as one utilizing an endoscopic instrument 35 (FIG. 3). By way of example but not limitation, endoscopic instrument 35 may comprise an endoscope carrying an extendable biopsy device 40 therein. Preferably deployable hoop expander 10 has an open lattice configuration allowing access to the side wall of the body lumen or body cavity. In one preferred form of the invention, deployable hoop expander 10 comprises a polygonal structure.

As will hereinafter be discussed in further detail, deployable hoop expander 10 is preferably also configured so as to allow an instrument (e.g., endoscopic instrument 35) to dock with deployable hoop expander 10, whereby to permit the deployable hoop expander to steady or stabilize the tip(s) or working end(s) of the instrument (or instruments).

Parallel rings 15 can have a circular configuration (in which case deployable hoop expander 10 will have a cylindrical configuration when expanded), an oval configuration (in which case deployable hoop expander 10 will have an ovoid shape when expanded), or other shapes which may be determined by the organ or cavity into which deployable hoop expander 10 is inserted, etc.

Furthermore, parallel rings 15 can have diameters which vary along the length of deployable hoop expander 10, such that the deployable hoop expander can form a particular non-cylindrical or non-ovoid geometry when it is in its expanded cross-sectional configuration. By way of example but not limitation, parallel rings 15 can have various diameters such that the deployable hoop expander expands into a spherical configuration.

Additionally, deployable hoop expander 10 can be closed at its distal end, and/or partially closed at its proximal end, and/or partially closed at its proximal and distal ends, if desired.

Preferably, the proximal end of deployable hoop expander 10 comprises one or more guides 45 for receiving the distal end of endoscopic instrument 35 relative to deployable hoop expander 10. Among other things, guides 45 can be configured so as to allow endoscopic instruments 35 to dock with deployable hoop expander 10, so that guides 45 can act to steady or stabilize endoscopic instruments 35 relative to deployable hoop expander 10 during an endoscopic procedure. In this respect it will be appreciated that providing a stable support platform for endoscopic instrument 35 can greatly facilitate stabilizing and aligning an instrument relative to the anatomy when conducting tissue inspection, biopsy and/or removal. This stable support platform can also enable and/or facilitate more extensive surgical procedures such as full thickness bowel resection (wall excision or segmental resection) and/or repair during intestinal procedures, peritoneal exploration (including natural orifice transendoscopic surgical procedures, which are sometimes referred to as NOTES), treatment of obstructions, and/or other complex endoscopic surgical procedures.

The expansible nature of deployable hoop expander 10 is such that it may be "sprung open" (i.e., transitioned from its reduced cross-sectional configuration to its expanded cross-sectional configuration) by a variety of means. Among other things, and as will hereinafter be discussed in further detail, deployable hoop expander 10 can be formed out of a spring material (e.g., a shape memory alloy such as Nitinol, a hardened stainless steel wire, a flexible plastic such as a self-expanding polymer, etc.) and constrained by an outer net; or deployable hoop expander 10 can be formed out of a spring material and constrained by an outer sheath; or deployable hoop expander 10 can be manipulated between its reduced cross-sectional configuration and its expanded cross-sectional configuration by manipulating control wires connected to struts 20; or by pinching one end of the device with a specialized tool, thereby elongating and narrowing the device, etc.

Figure 4:
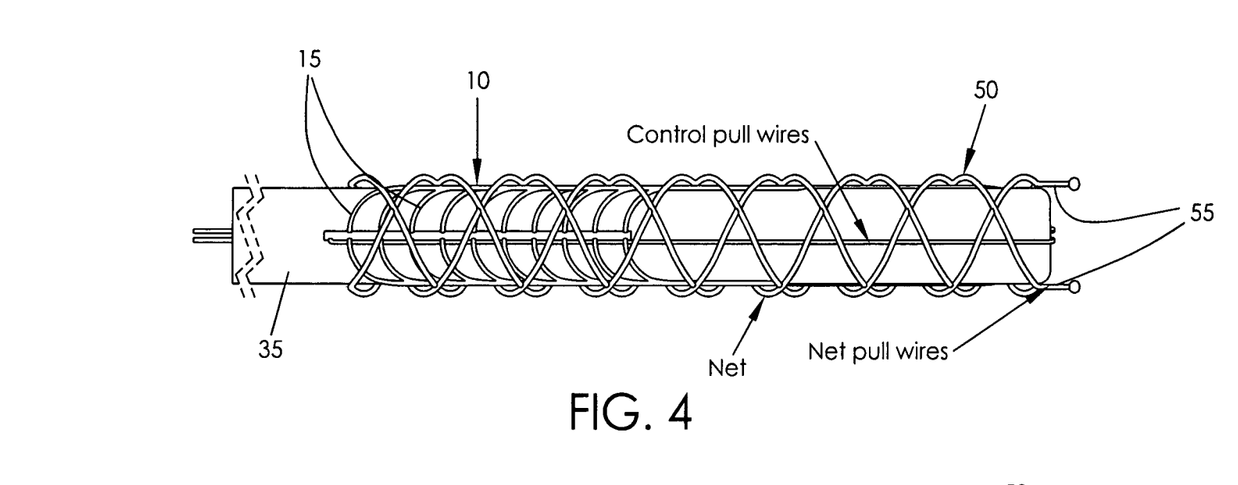
FIGS. 4-12 are schematic views showing various aspects of a novel endoscopic device comprising a deployable hoop expander formed out of spring material and constrained by an outer net.
Figure 5:
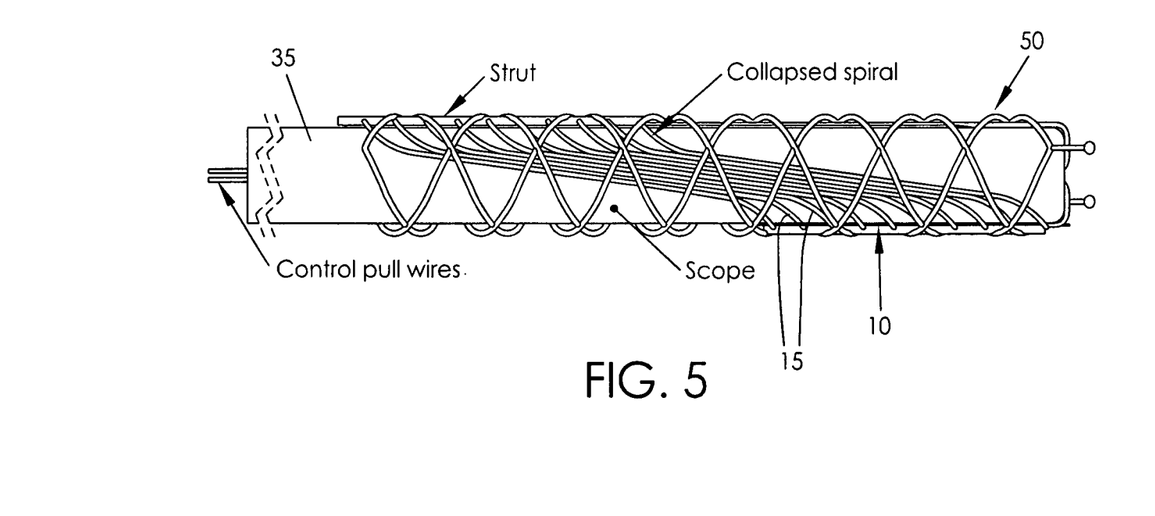
Figure 6:
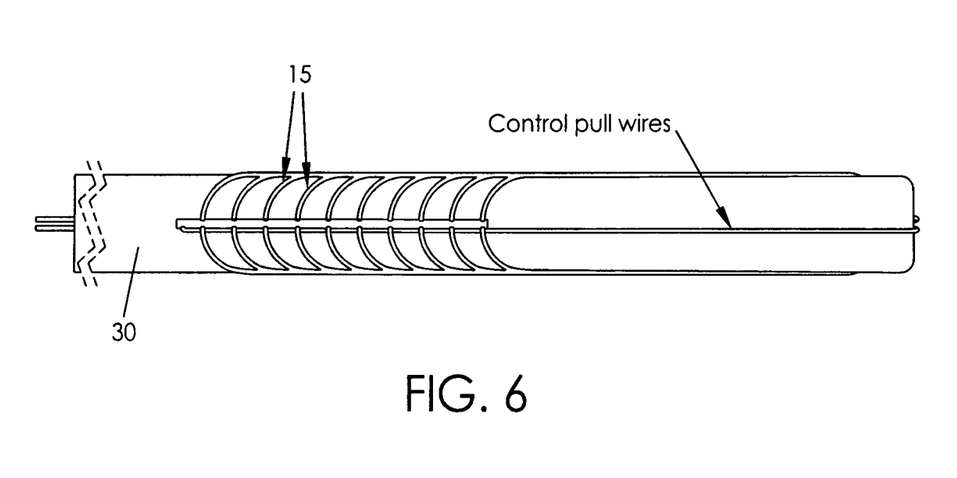
Figure 7:
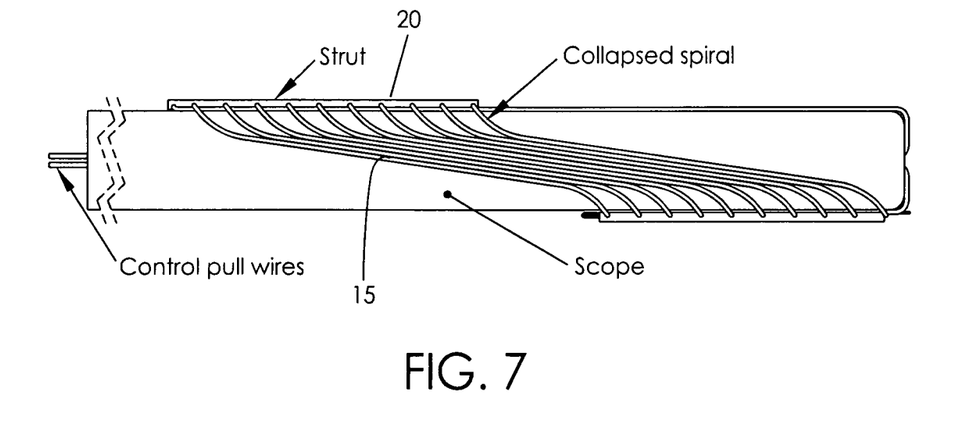
Figure 8:
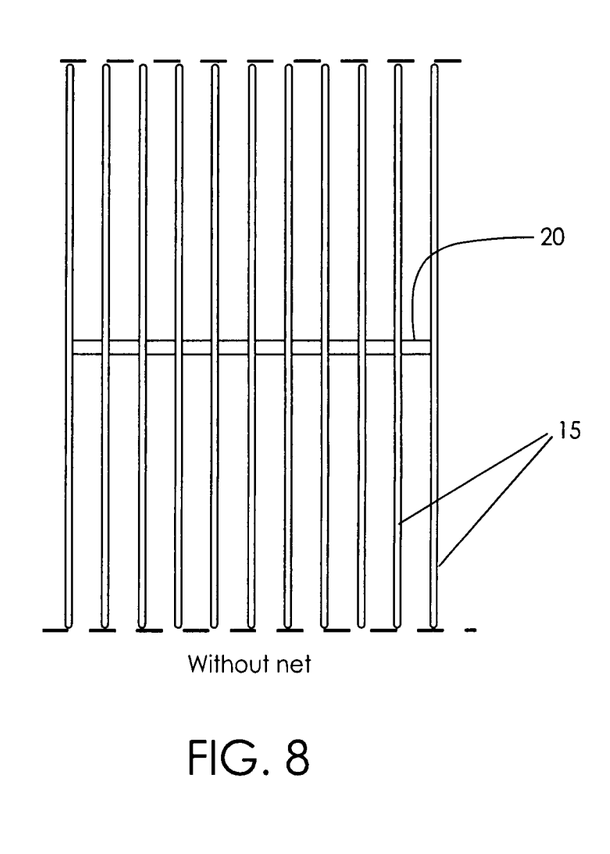

Deployable Hoop Expander Formed Out of Spring Material and Constrained by an Outer Net More particularly, and looking now at FIGS. 4 and 5, there is shown a configuration in which parallel rings 15 of deployable hoop expander 10 are formed out of a spring material (e.g., a shape memory alloy such as Nitinol, a hardened stainless steel wire, a flexible plastic such as a self-expanding polymer, etc.) and constrained by an outer net 50. In one preferred form of the invention, deployable hoop expander 10 is mounted over endoscopic instrument 35, with deployable hoop expander 10 being maintained in its reduced cross-sectional configuration using outer net 50. Alternatively, deployable hoop expander 10 may be maintained in its reduced cross-sectional configuration via outer net 50 and the entire assembly delivered through a lumen of endoscopic instrument 35; or deployable hoop expander 10 may be inserted alongside of, or entirely separately from, endoscopic instrument 35. In any case, in use, after deployable hoop expander 10 has been delivered to the therapeutic site, the net is withdrawn by pulling the net pull wires 55 (FIGS. 6 and 7), thereby exposing and releasing parallel rings 15. Upon net removal, parallel rings 15 automatically expand (FIG. 8) so as to engage the side wall of the body lumen and thereby expose, straighten and flatten the side wall tissue. At the conclusion of the procedure, deployable hoop expander 10 may be returned to its reduced cross-sectional configuration and removed from the body lumen, or it may under certain circumstances remain in place.

Figure 9:
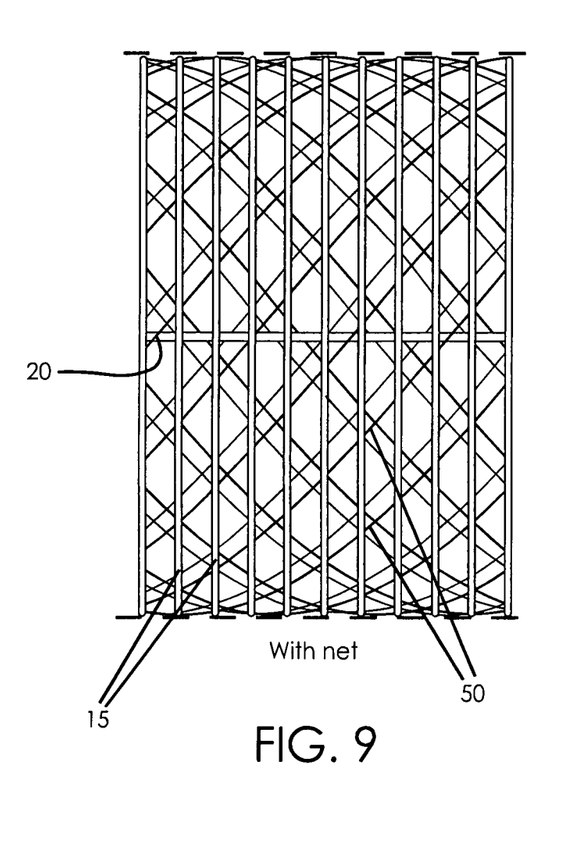
Figure 10:
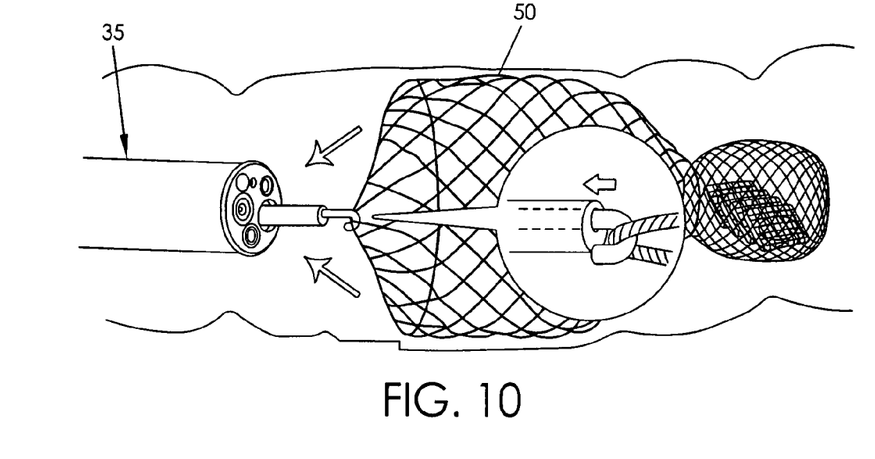
Figure 11:
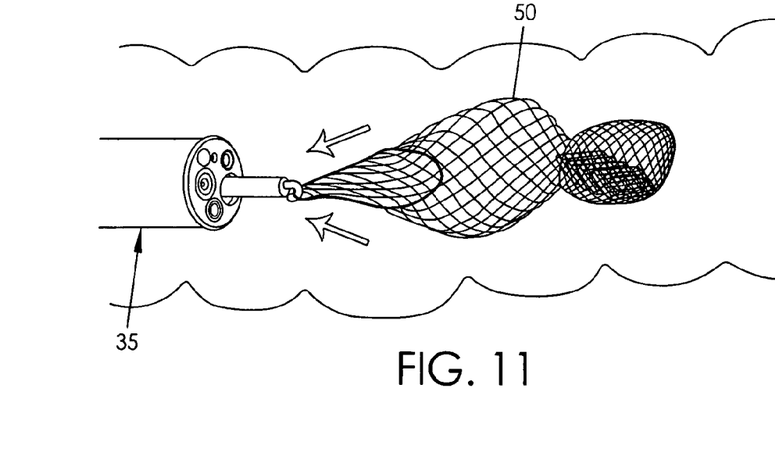
Figure 12:
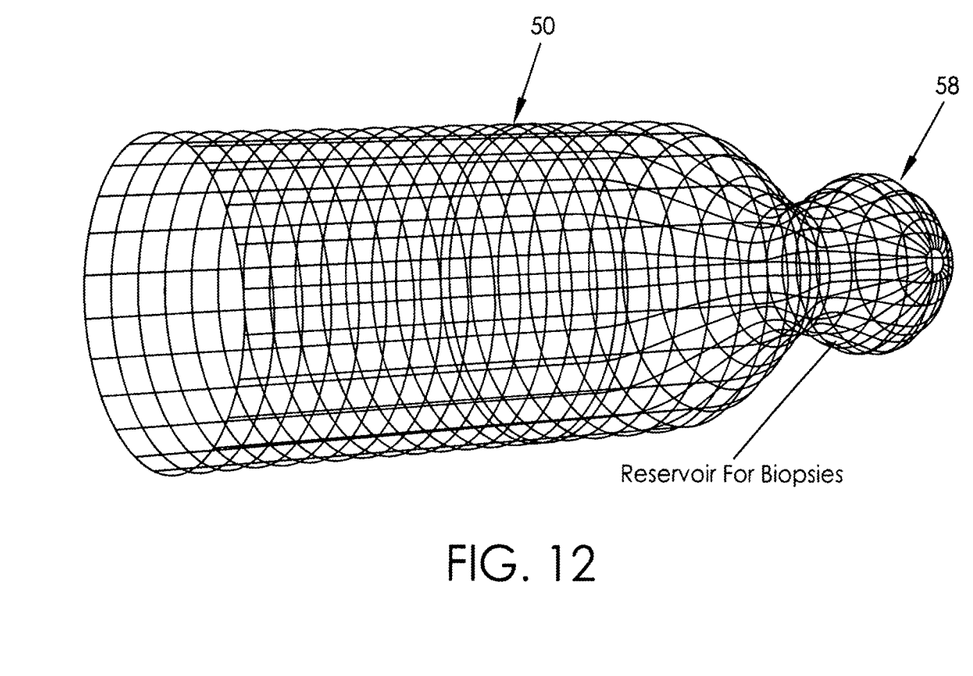

In another form of the present invention, and looking now at FIGS. 9-11, net 50 may be loosened so as to release the restrained deployable hoop expander 10, thereby allowing parallel rings 15 to expand, but the net is still kept in place around the expanded deployable hoop expander (FIG. 9). As a result, by forming net 50 with a closed distal end, the net can sit as a "trap" about the therapeutic site so as to catch and retain anything which may be removed or dislodged from the side wall of the body lumen during a procedure. Thereafter, at the conclusion of the procedure, deployable hoop expander 10 can be returned to its reduced cross-sectional configuration and removed from the body lumen, and then net 50 can be withdrawn from the body lumen (FIGS. 10 and 11), carrying with it any tissue or debris removed from the side wall of the body lumen and entrapped by the net. In this form of the invention, it may be desirable to form net 50 with a distal end reservoir 58 (FIG. 12) for storing excised tissue (e.g., biopsy specimens) or dislodged debris.

Figure 13:
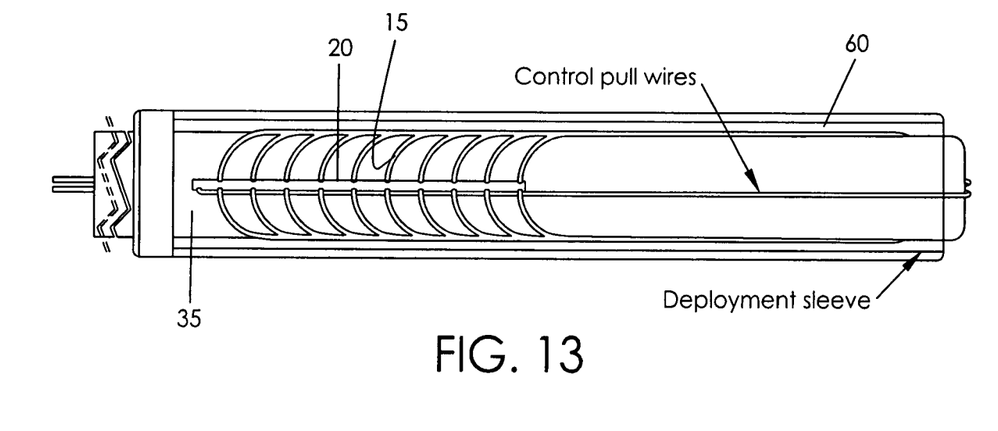
FIGS. 13 and 14 are schematic views showing various aspects of a novel endoscopic device comprising a deployable hoop expander formed out of spring material and constrained by an outer sleeve.
Figure 14:
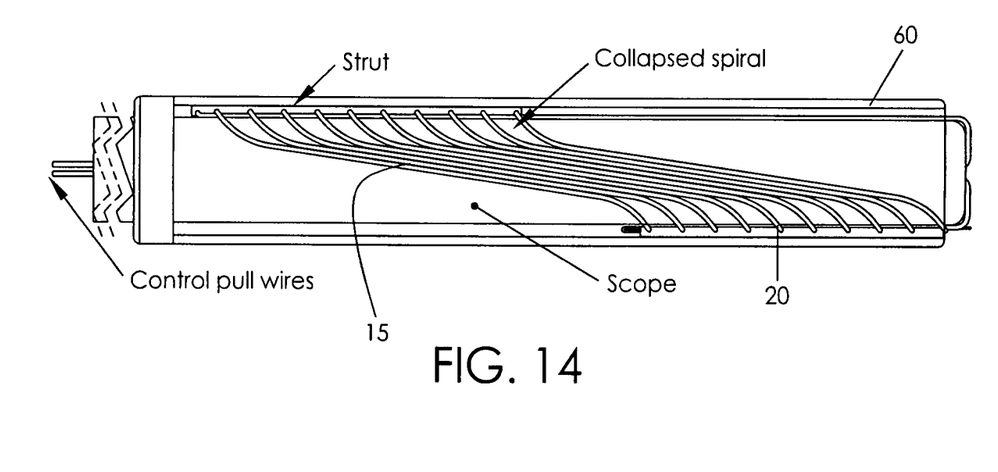

Deployable Hoop Expander Formed Out of Spring Material and Constrained by an Outer Sleeve In another form of the invention, and looking now at FIGS. 13 and 14, there is provided a configuration in which deployable hoop expander 10 is formed out of a spring material (e.g., a shape memory alloy such as Nitinol, a hardened stainless steel wire, a flexible plastic such as a self-expanding polymer, etc.) and constrained by an outer sleeve 60. In one preferred form of the invention, deployable hoop expander 10 is mounted over endoscopic instrument 35, with deployable hoop expander 10 being maintained in its reduced cross-sectional configuration using outer sleeve 60. Alternatively, deployable hoop expander 10 may be maintained in its reduced cross-sectional configuration via outer sleeve 60 and the entire assembly delivered through a lumen of endoscopic instrument 35. Or deployable hoop expander 10 may be inserted alongside of, or entirely separately from, endoscopic instrument 35. In any case, in use, after deployable hoop expander 10 has been delivered to the therapeutic site, the outer sleeve is removed, thereby releasing parallel rings 15. With outer sleeve 60 removed, parallel rings 15 automatically expand so as to engage the side wall of the body lumen and straighten and flatten the same.

Deployable Hoop Expander Erected with Control Wires

Figure 15:
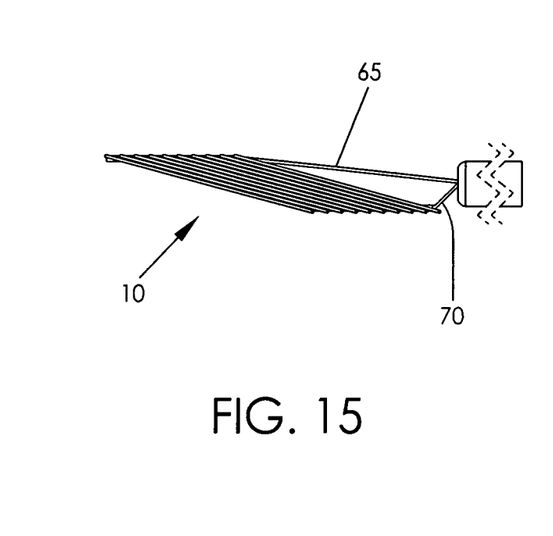
FIGS. 15-17 are schematic views showing various aspects of a novel endoscopic device comprising a deployable hoop expander erected with control wires.
Figure 16:
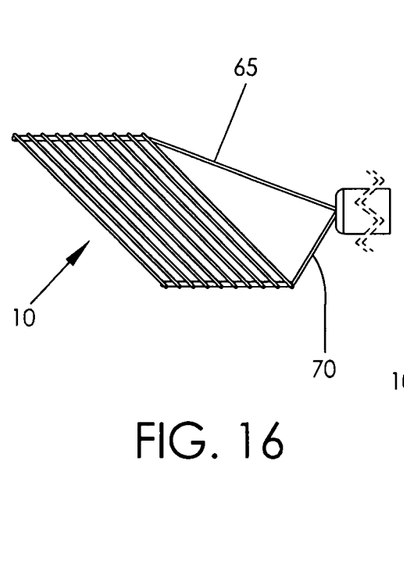
Figure 17:
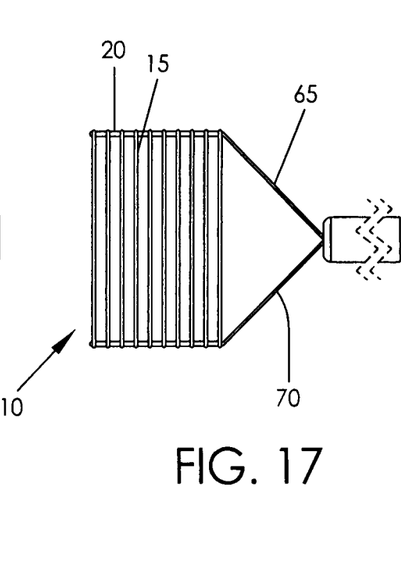

Looking next at FIGS. 15-17, there is shown a configuration in which deployable hoop expander 10 can be manipulated by control wires 65, 70 connected to struts 20 so as to expand parallel rings 15. In one preferred form of the invention, deployable hoop expander 10 is mounted over an endoscopic instrument (not shown in FIGS. 15-17), with the deployable hoop expander being maintained in its reduced cross-sectional configuration. Alternatively, deployable hoop expander 10 could be delivered through a lumen of an endoscopic instrument, again with the deployable hoop expander being maintained in its reduced cross-sectional configuration. Or deployable hoop expander 10 may be inserted alongside of, or entirely separately from, an endoscopic instrument. In any case, in use, after deployable hoop expander 10 has been delivered to the therapeutic site, the deployable hoop expander is erected by pulling distally on control wire 65. This action erects the deployable hoop expander so that it assumes its expanded cross-sectional configuration (see FIGS. 15-17). Significantly, in this form of the invention, deployable hoop expander 10 does not need to be formed out of a resilient material, since the deployable hoop expander is erected by pulling on control wire 65, and is not erected by the resilient nature of the deployable hoop expander itself.

Additionally, deployable hoop expander 10 can be collapsed by releasing the previously-pulled control wire 65. Deployable hoop expander 10 can then be moved by pulling on both control wires 65, 70. Once deployable hoop expander has been properly re-positioned, it can be expanded again simply by pulling on control wire 65.

It should be appreciated that, in the configurations shown in FIGS. 15-17, struts 20 are preferably connected to parallel rings 15 with a hinge arrangement which allows the struts to pivot relative to parallel rings 15. This hinge could be a pinned hinge, a living hinge, etc.

Forming the Deployable Hoop Expander with a Helical Construction

In another form of the invention, deployable hoop expander 10 may be formed with a helical construction. More particularly, in this form of the invention, the plurality of parallel rings 15 may be replaced by a helix, a double helix, another form of spiral, or another collapsible/expandable polygonal structure defining a volume. Where deployable hoop expander 10 is formed out of a helix, double helix or another form of spiral, struts 20 may or may not be provided.

Regardless of the particular construction chosen for the deployable hoop expander, preferably at least a portion of the deployable hoop expander has an open configuration (e.g., an open lattice configuration) allowing access to the side wall of the body lumen or body cavity.

Figures 18, 19, 20:
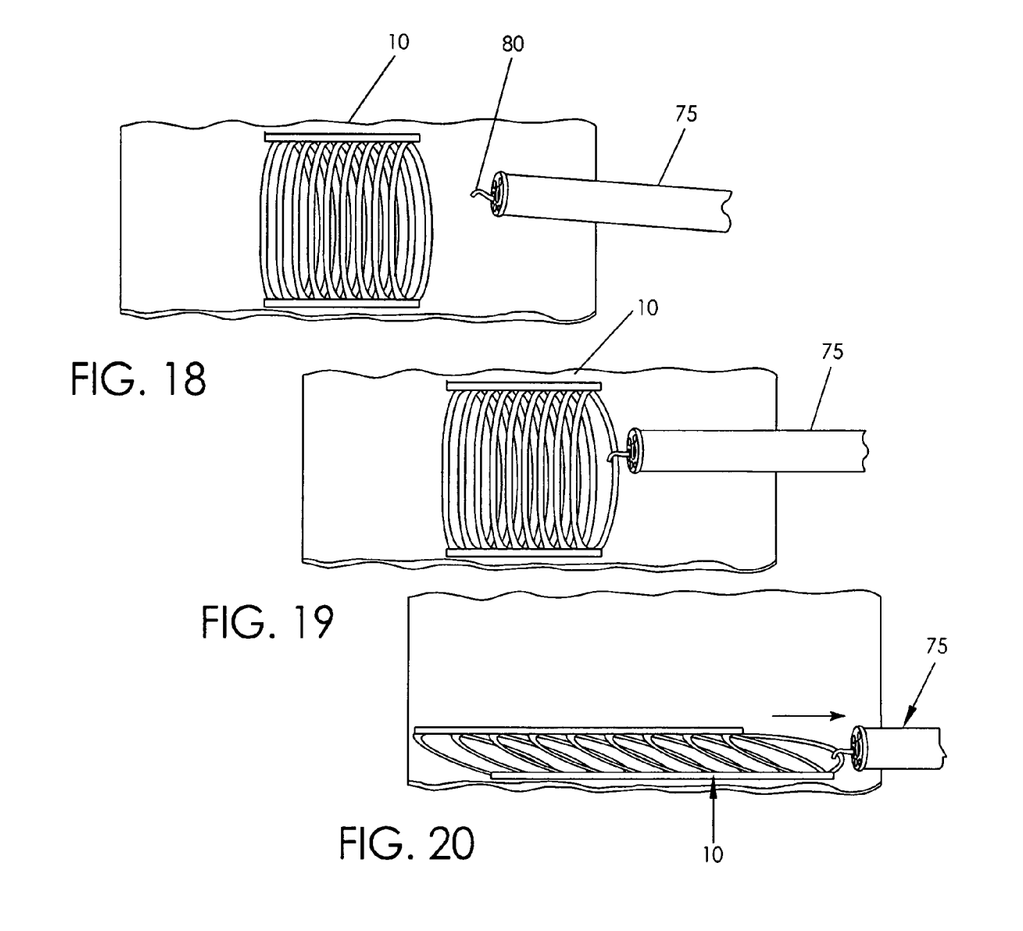
FIGS. 18-20 are schematic views showing the use of a grasping tool for repositioning or removing the deployable hoop expander.

Use of Grasping Tool for Re-Positioning or Removing the Deployable Hoop Expander Looking next at FIGS. 18-20, deployable hoop expander 10 may also be retracted (e.g., for re-positioning or complete removal) with a specialized grasping tool 75. More particularly, specialized grasping tool 75 comprises a hook 80 which can grasp the end-most parallel ring 15 of the deployable hoop expander so as to cause the entire device to elongate and narrow, thereby making it re-positionable or removable.

Delivery of the Deployable Hoop Expander Vis-à-vis an Endoscope or Other Device

Figure 21:
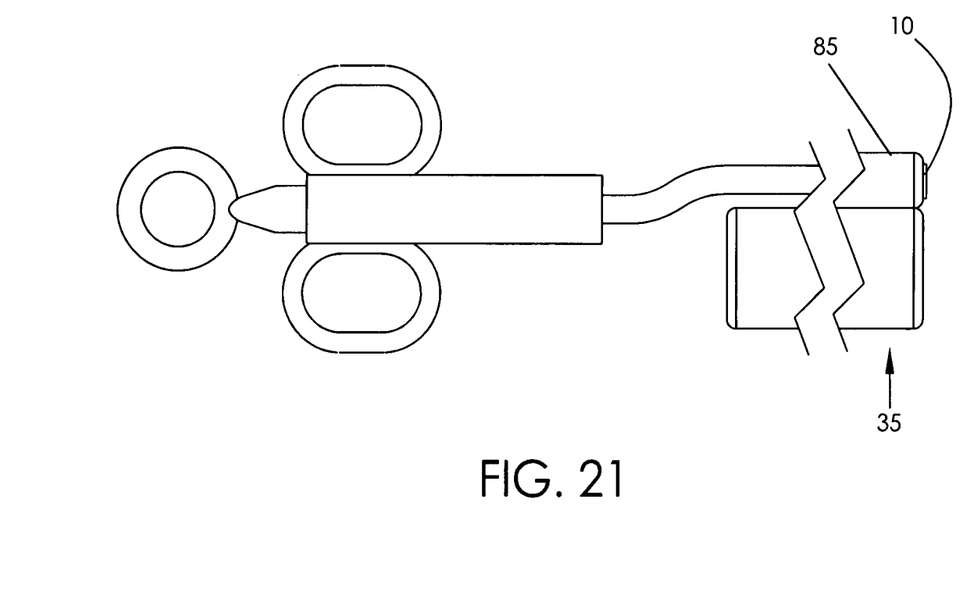
FIGS. 21 and 22 are schematic views showing delivery of the deployable hoop expander vis-à-vis an endoscope or other device.
Figure 22:
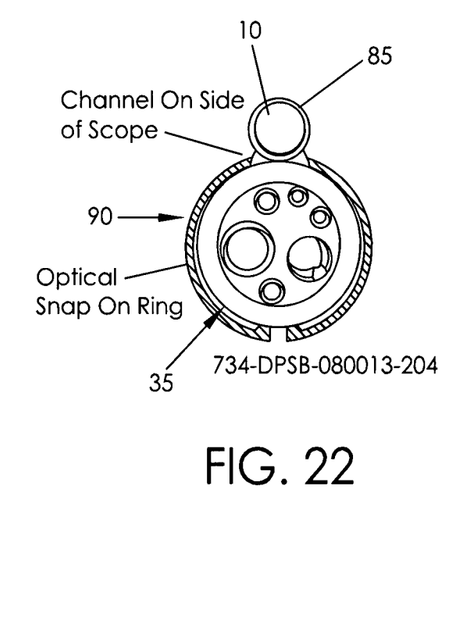

As noted above, deployable hoop expander 10 is designed such that it can be delivered over an endoscope or other instrument, or through the working channel of an endoscope or other instrument, or it can be delivered alongside an endoscope or other instrument, or entirely outside of or separate from an endoscope or other instrument. See, for example, FIGS. 21 and 22, which show deployable hoop expander 10 disposed in a channel 85 disposed parallel to endoscopic instrument 35. Channel 85 may be affixed to endoscopic instrument 35 in various ways, e.g., with an optional snap-on ring 90.

Maintaining the Deployable Hoop Expander in the Body at the Conclusion of an Endoscopic Procedure It is anticipated that, in most cases, deployable hoop expander 10 will be removed from the patient at the conclusion of the endoscopic procedure. However, in some cases it may be desirable to provide support to the vessel or organ for some period of time after the conclusion of the endoscopic procedure. In this case, deployable hoop expander 10 may be left in the body lumen at the conclusion of the procedure and thereafter, when support is no longer required, the deployable hoop expander can be removed from the body. Optionally, deployable hoop expander 10 can be formed out of a biodegradable/absorbable material. In this case, the device can be left in the body at the conclusion of the endoscopic procedure, whereupon it will thereafter biodegrade or be absorbed by the body.

Applications

The novel endoscopic/surgical device of the present invention can be used in substantially any endoscopic or surgical procedure to facilitate the alignment and presentation of tissue during an endoscopic procedure or to fix, dock, or stabilize the working end of an endoscope or other instrument during such a procedure.

The present invention is believed to have widest applications with respect to the gastrointestinal (GI) tract, which is generally characterized by frequent turns and which has a side wall characterized by numerous folds. However, the methods and apparatus of the present invention may also be used inside other body cavities (e.g., the cranium, thorax, abdomen, pelvis, nasal sinuses, chest, bladder, etc.) and other tubular viscera (e.g., the esophagus, stomach, duodenum, vagina, ureter, fallopian tubes, urethra, blood vessels, bronchi, etc.).

Thus, for example, the novel endoscopic device of the present invention can be used in the performance of certain specialized endoscopic procedures including Natural Orifice Trans-Endoscopic Surgery (NOTES) procedures, as well as other complex endoscopic procedures which could involve endoscopic surgery.

Modifications

While the present invention has been described in terms of certain exemplary preferred embodiments, it will be readily understood and appreciated by one of ordinary skill in the art that it is not so limited, and that many additions, deletions and modifications may be made to the preferred embodiments discussed above while remaining within the scope of the present invention.

What is claimed is:

1. An apparatus for straightening and flattening a side wall of a body lumen or body cavity, so as to provide three dimensional exposure of, and access to, a lesion or abnormality within the body lumen or body cavity during an endoscopic procedure, the apparatus comprising:
   an endoscope having a distal end for insertion into the body lumen or body cavity, and a proximal end for disposition outside of the body lumen or body cavity;

a deployable hoop expander comprising a distal end, a proximal end and a longitudinally-extending outer perimeter extending therebetween, the longitudinally-extending outer perimeter being delineated by an open lattice structure and defining a volume;

the deployable hoop expander being configured so as to be transitionable between (i) a reduced cross-sectional configuration, and (ii) an expanded cross-sectional configuration, whereby the deployable hoop expander can be configured in its reduced cross-sectional configuration for easy insertion into a body lumen, and it can thereafter be re-configured into its expanded cross-sectional configuration so as to engage, straighten and flatten the side wall of the body lumen, whereby to provide three dimensional exposure of, and access to, the lesion or abnormality through the open lattice structure, the entire deployable hoop expander being configured for disposition within the body lumen or body cavity;

the proximal end of the deployable hoop expander comprising at least one guide for releasably mounting the deployable hoop expander to the distal end of the endoscope such that the distal end of the endoscope is supported and stabilized relative to the body lumen or body cavity when the deployable hoop expander is in its expanded cross-sectional configuration within the body lumen or body cavity;

wherein the open lattice structure is sized so that a working instrument may be passed through the endoscope and access the lesion or abnormality through the open lattice structure; and wherein the at least one guide is configured so that the deployable hoop expander can be selectively released from the distal end of the endoscope, whereby to dismount the deployable hoop expander from the endoscope so that the deployable hoop expander may be left in the body lumen or body cavity when the endoscope is removed from the body at the conclusion of the endoscopic procedure, with the entire deployable hoop expander being disposed in the body lumen or body cavity.

2. The apparatus according to claim 1 wherein the deployable hoop expander comprises a polygonal structure.

3. The apparatus according to claim 1 wherein the open lattice structure comprises a plurality of parallel rings connected to one another by at least one strut.

4. The apparatus according to claim 3 wherein the parallel rings have a circular configuration.

5. The apparatus according to claim 3 wherein the parallel rings have an ovoid configuration.

6. The apparatus according to claim 3 wherein the parallel rings have diameters which vary along the length of the deployable hoop expander, such that the deployable hoop expander can form a non-cylindrical and non-ovoid geometry when it is in its expanded cross-sectional configuration.

7. The apparatus according to claim 6 wherein the deployable hoop expander has a spherical configuration.

8. The apparatus according to claim 3 wherein:
(i) when the deployable hoop expander is in its reduced cross-sectional configuration, the planes of the parallel rings are disposed at an acute angle (when seen in side view) to the longitudinal axis of the deployable hoop expander; and
(ii) when the deployable hoop expander is in its expanded cross-sectional configuration, the planes of the parallel rings are disposed perpendicular (when seen in side view) to the longitudinal axis of the deployable hoop expander.

9. The apparatus according to claim 1 wherein the open lattice structure comprises a spiral construction.

10. The apparatus according to claim 9 wherein the spiral construction comprises a helix.

11. The apparatus according to claim 9 wherein the spiral construction comprises a helix and at least one strut.

12. The apparatus according to claim 1 wherein the deployable hoop expander is resilient and is normally biased into its expanded cross-sectional configuration, and further wherein the apparatus comprises a constraint for maintaining the deployable hoop expander in its reduced cross-sectional configuration.

13. The apparatus according to claim 12 wherein the constraint comprises a net.

14. The apparatus according to claim 13 wherein one end of the net is closed.

15. The apparatus according to claim 12 wherein the constraint comprises a sleeve.

16. The apparatus according to claim 1 wherein the open lattice structure is characterized by a parallelogram configuration when seen in side view, and further wherein the apparatus comprises a control wire for manipulating the deployable hoop expander from its reduced cross-sectional configuration to its expanded cross-sectional configuration.

17. The apparatus according to claim 16 wherein the open lattice structure comprises a plurality of parallel rings connected to one another by at least one strut.

18. The apparatus according to claim 17 wherein the at least one strut is connected to the parallel rings by hinges.

19. The apparatus according to claim 1 wherein the distal end of the deployable hoop expander is closed.

20. The apparatus according to claim 1 wherein the proximal end of the deployable hoop expander is partially closed.

21. The apparatus according to claim 1 wherein the apparatus further comprises a grasping tool for collapsing and removing the deployable hoop expander.

22. The apparatus according to claim 1 wherein the deployable hoop expander comprises a biocompatible material.

23. The apparatus according to claim 22 wherein the biocompatible material is a biodegradable/absorbable material.

24. The apparatus according to claim 1 wherein the deployable hoop expander comprises a superelastic alloy material.

25. The apparatus according to claim 1 wherein the deployable hoop expander comprises a shape memory alloy material.

26. The apparatus according to claim 1 wherein the deployable hoop expander comprises a polymeric material.

27. The apparatus according to claim 1 wherein the deployable hoop expander is configured to be passed through the biopsy channel of an endoscope.

28. The apparatus according to claim 1 wherein the deployable hoop expander is configured to be passed over the outside of an endoscope.

29. A method for straightening and flattening a side wall of a body lumen or body cavity so as to provide three dimensional exposure of, and access to, a lesion or abnormality on the side wall within the body lumen or body cavity during an endoscopic procedure, the method comprising:
providing apparatus comprising:

an endoscope having a distal end for insertion into the body lumen or body cavity, and a proximal end for disposition outside of the body lumen or body cavity;

a deployable hoop expander comprising a distal end, a proximal end and a longitudinally-extending outer perimeter extending therebetween, the longitudinally-extending outer perimeter being delineated by an open lattice structure and defining a volume;

the deployable hoop expander being configured so as to be transitionable between (i) a reduced cross-sectional configuration, and (ii) an expanded cross-sectional configuration, the entire deployable hoop expander being configured for disposition within the body lumen or body cavity; and the proximal end of the deployable hoop expander comprising at least one guide for releasably mounting the deployable hoop expander to the distal end of the endoscope such that the distal end of the endoscope is supported and stabilized relative to the body lumen or body cavity when the deployable hoop expander is in its expanded cross-sectional configuration within the body lumen or body cavity;

wherein the open lattice structure is sized so that a working instrument may be passed through the endoscope and access the lesion or abnormality on the side wall through the open lattice structure; and wherein the at least one guide is configured so that the deployable hoop expander can be selectively released from the distal end of the endoscope, whereby to dismount the deployable hoop expander from the endoscope so that the deployable hoop expander may be left in the body lumen or body cavity when the endoscope is removed from the body at the conclusion of the endoscopic procedure, with the entire deployable hoop expander being disposed in the body lumen or body cavity;

configuring the deployable hoop expander in its reduced cross-sectional configuration;

mounting the deployable hoop expander to the distal end of the endoscope via the at least one guide;

advancing the deployable hoop expander into a body lumen or body cavity;

re-configuring the deployable hoop expander into its expanded cross-sectional configuration so as to engage, straighten and flatten the side wall of the body lumen or body cavity, whereby to provide three dimensional exposure of, and access to, the lesion or abnormality through the open lattice structure and stabilizing the distal end relative to the side wall of the body lumen or body cavity when the deployable hoop expander is in the expanded cross-sectional configuration;

passing a working instrument through the endoscope;

accessing the lesion or abnormality with the working instrument during the endoscopic procedure through the open lattice structure;

dismounting the deployable hoop expander from the distal end of the endoscope by releasing the at least one guide from the distal end of the endoscope; and withdrawing the endoscope from the body lumen or body cavity, leaving the deployable hoop expander disposed entirely within the body lumen or body cavity.

30. The method according to claim 29 wherein the method comprises the additional steps of:

re-configuring the deployable hoop expander into its reduced cross-sectional configuration; and removing the deployable hoop expander from the body lumen or body cavity.

31. The method according to claim 29 wherein the deployable hoop expander comprises a polygonal structure.

32. The method according to claim 29 wherein the deployable hoop expander is resilient and is normally biased into its expanded cross-sectional configuration, and further wherein the deployable hoop expander comprises a constraint for maintaining the deployable hoop expander in its reduced cross-sectional configuration.

33. The method according to claim 32 wherein the deployable hoop expander is (i) configured in its reduced cross-sectional configuration by compressing the deployable hoop expander and then applying the constraint so as to maintain the deployable hoop expander in its reduced cross-sectional configuration; and (ii) re-configured into its expanded cross-sectional configuration by releasing the constraint.

34. The method according to claim 33 wherein the constraint comprises a net.

35. The method according to claim 34 wherein the constraint is released by removing the net.

36. The method according to claim 34 wherein the constraint is released by relaxing the net.

37. The method according to claim 33 wherein the constraint comprises an outer sleeve.

38. The method according to claim 37 wherein the constraint is released by removing the outer sleeve.

39. The method according to claim 29 wherein the deployable hoop expander is characterized by a parallelogram configuration when seen in side view, and further wherein the deployable hoop expander comprises a control wire for manipulating the deployable hoop expander from its reduced cross-sectional configuration to its expanded cross-sectional configuration.

40. The method according to claim 39 wherein the deployable hoop expander is (i) configured in its reduced cross-sectional configuration by collapsing the parallelogram configuration; and (ii) re-configured into its expanded cross-sectional configuration by manipulating the control wire.

41. The method according to claim 29 wherein the deployable hoop expander comprises a plurality of parallel rings connected to one another by at least one strut, and further wherein:

(i) when the deployable hoop expander is in its reduced cross-sectional configuration, the planes of the parallel rings are disposed at an acute angle (when seen in side view) to the longitudinal axis of the deployable hoop expander; and (ii) when the deployable hoop expander is in its expanded cross-sectional configuration, the planes of the parallel rings are disposed perpendicular (when seen in side view) to the longitudinal axis of the deployable hoop expander.

* * * * *